United States Patent [19]

Lazik et al.

[11] Patent Number: 4,726,748

[45] Date of Patent: Feb. 23, 1988

[54] APPARATUS FOR REPLICATION OF BLOOD VESSELS AND DUCTAL ORGANS

[76] Inventors: Arthur J. Lazik, 18350 Roscoe Blvd., Northridge, Calif. 91325; Norman V. Petersen, 19930 Lubao Pl., Chatsworth, Calif. 91311; T. Douglas Petersen, 8220 Owensmouth Ave., Canoga Park, Calif. 91304

[21] Appl. No.: 869,707

[22] Filed: Jun. 2, 1986

[51] Int. Cl.⁴ .............................................. B29C 45/17
[52] U.S. Cl. ...................................... 425/2; 264/221; 264/222
[58] Field of Search ..................... 425/2, 12, 87, 458; 264/222, DIG. 30; 128/321, 346; 434/81, 272, 275; 264/221

[56] References Cited

U.S. PATENT DOCUMENTS

| | | | |
|---|---|---|---|
| 2,937,443 | 5/1960 | Skinner | 264/222 |
| 3,063,455 | 11/1962 | Markley | 128/321 |
| 3,926,195 | 12/1975 | Bleier et al. | 128/321 |
| 4,312,826 | 1/1982 | Colvin | 264/222 |
| 4,385,015 | 5/1983 | Klettke | 425/12 |

OTHER PUBLICATIONS

Walburn et al, "Constructions of Molds of Complex Arterial Segments", Journal of Biomechanical Engineering, vol. 102, No. 4 (Nov. 1980), pp. 284–286.

Primary Examiner—Jay H. Woo
Assistant Examiner—James C. Housel
Attorney, Agent, or Firm—Gilbert Kivenson

[57] ABSTRACT

An apparatus for obtaining a pressure tight seal around the ostium of a blood vessel branch by clamping to the parent blood vessel or duct wall without deforming the branch. The apparatus may then be used for the injection of a hardenable material such as a polymerizable liquid plastic or a hardenable radiopaque liquid. When the blood vessel or duct is completely filled and the injected material has hardened, the original blood vessel or duct tissue can be removed by corrosion. An accurate replica of the blood vessel or duct is then obtained. The replica may be studied as part of a postmortem examination or used for instruction. If the radiopaque liquid has been used, the replica may be studied by the use of x-rays.

5 Claims, 6 Drawing Figures

APPARATUS FOR REPLICATION OF BLOOD VESSELS AND DUCTAL ORGANS

INTRODUCTION

The present invention relates to an apparatus which will permit postmortem pressure injection of a hardenable, corrosion resistant or radiopaque liquid selectively into the ostium (opening) of a blood vessel or duct, both hereafter referred to as a tube, at its branchpoint off the parent or another blood vessel or duct without deforming the tube. The latter may be either entering or exiting from the desired biologic organ which remains in situ or has been removed from the body. The hardenable, corrosion resistant liquid forms a cast of the injected tubular system which can then be studied in detail visually and microscopically after all the biologic tissues including the tube wall have been removed by corrosion. If the radiopaque liquid is used, it forms a replica of the tubular system which can then be studied by the use of x-ray photography.

The invention may also be used for selective and simultaneous injection of two or more tubes of the same biologic organ using different color injectates so that each tube and its intercommunications are identifiable by color code. The present invention replaces and is superior to two practices in the prior art:

a. direct introduction of a cannula through the ostium into a tube and then securing the cannula in place by ligation. This practice distorts the structure being cannulated, allows replication of the structure only beyond the cannula and omits from the replica the ostium and any branch structures between the ostium and the cannula tip.

b. Positioning an injection outlet in proximity to the ostium of the tube—a technique which allows only semi-selective injection and may lead to undesirable runoff of one color of hardenable, corrosion resistant or radiopaque liquid into the ostium of adjacent tubes of the same biologic organ.

It is an objective of the present invention to produce a more complete replica by introducing liquid injectates directly into a confined area around the ostium of a tube leading to or from an organ thereby including the ostium and the transitional part of the parent blood vessel or duct.

It is a second objective of the present invention to provide a means for mechanically, rapidly and effectively sealing the injection apparatus around the ostium of a tube without the use of ligating or adhesive methods.

It is a third objective of the present invention to provide a means for sealing the injection apparatus selectively around the ostium of a tube so that only the desired tube of the organ is filled while other tubes of the same organ may be similarly and simultaneously filled with liquid injectates of different colors. Differentiation of one vascular system from another or one ductal system from another is thus achieved by differences in color.

These and other objectives will be explained with reference to the accompanying drawings.

DESCRIPTION OF THE INVENTION

Figure 1:
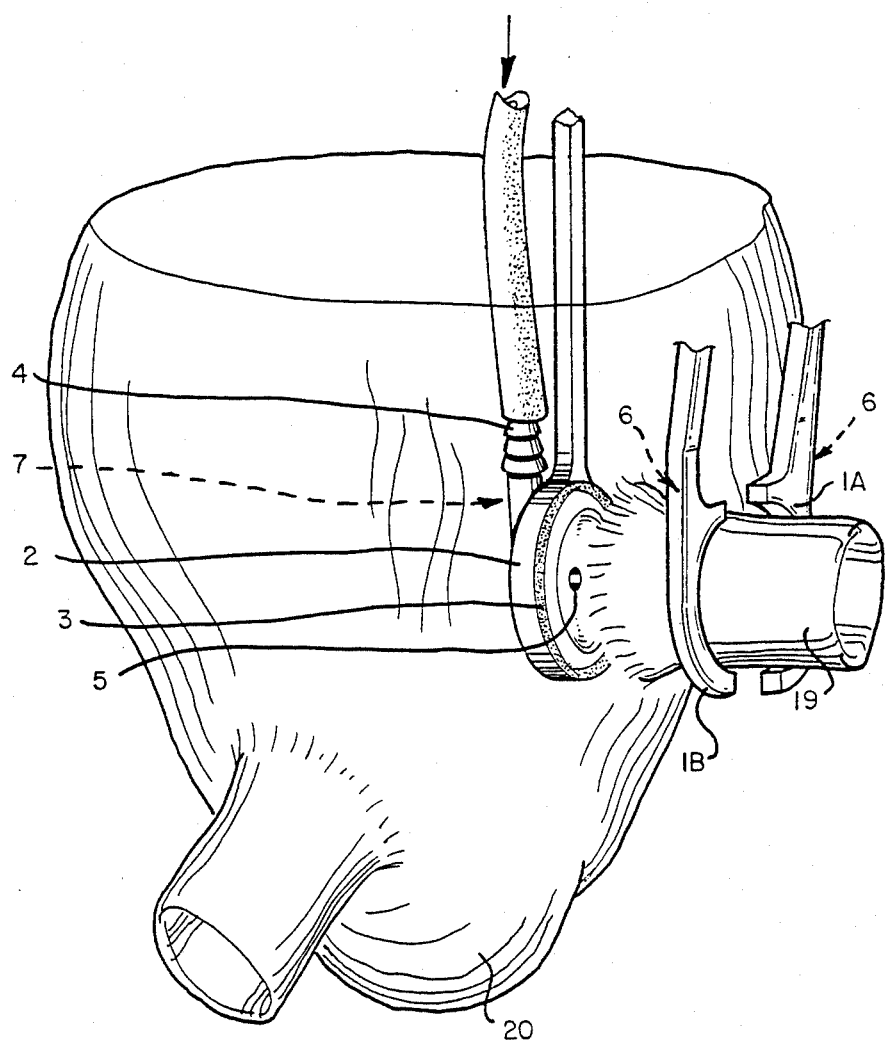
FIG. 1 illustrates the clamping and injection elements of the invention and shows how these are applied around the ostium of a tube branching off the parent blood vessel or duct entering or exiting from an organ, in a first embodiment of the invention.

Referrring now to FIG. 1, the ring segments 1A and 1B are brought together in the direction 6 and clamped around the tube 19. The tube in this case is the blood vessel or duct of the main organ selected for injection. The chamber 2, incorporating the flexible sealing ring 3, the serrated inlet pipe 4 and the opening 5 is next moved in the direction 7 which is orthogonal to the clamping plane of the ring segments 1A and 1B. A seal is obtained around the opening of the parent wall 20 of the tube 19 by forcing sealing ring 3 against the closed toroidal ring 1A–1B and trapping the parent wall 20 in between as shown in FIG. 2a. A hardenable, corrosion resistant or radiopaque liquid can now be injected under pressure into the tube 19 by way of its ostium without deforming the ostium or tube. The seal permits the maintenance of injection pressure thereby allowing the injected liquid to fill the entire bores of the tube as well as its major and minor branches from the tube ostium to the tube termination. Upon hardening, followed by acid or alkali immersion, there is produced a detailed model of the desired organ. Examples of cases where this might be desired would be: the postmortem study of the coronary arteries and aorto-coronary saphenous vein bypass grafts at their take-off from the aorta; the study of internal mammary arteries at their take-off from the subclavian arteries.

Figure 2A:
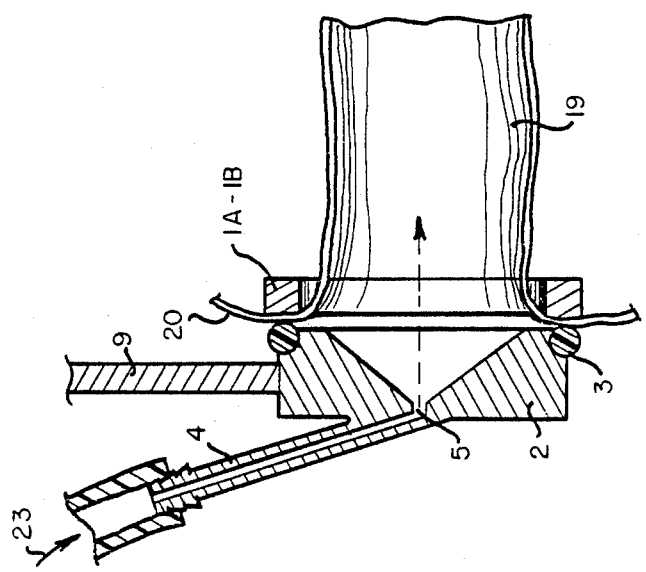
FIG. 2a is a cross-section of the elements of FIG. 1, illustrating the clamping and injecting functions of the invention.
Figure 3:
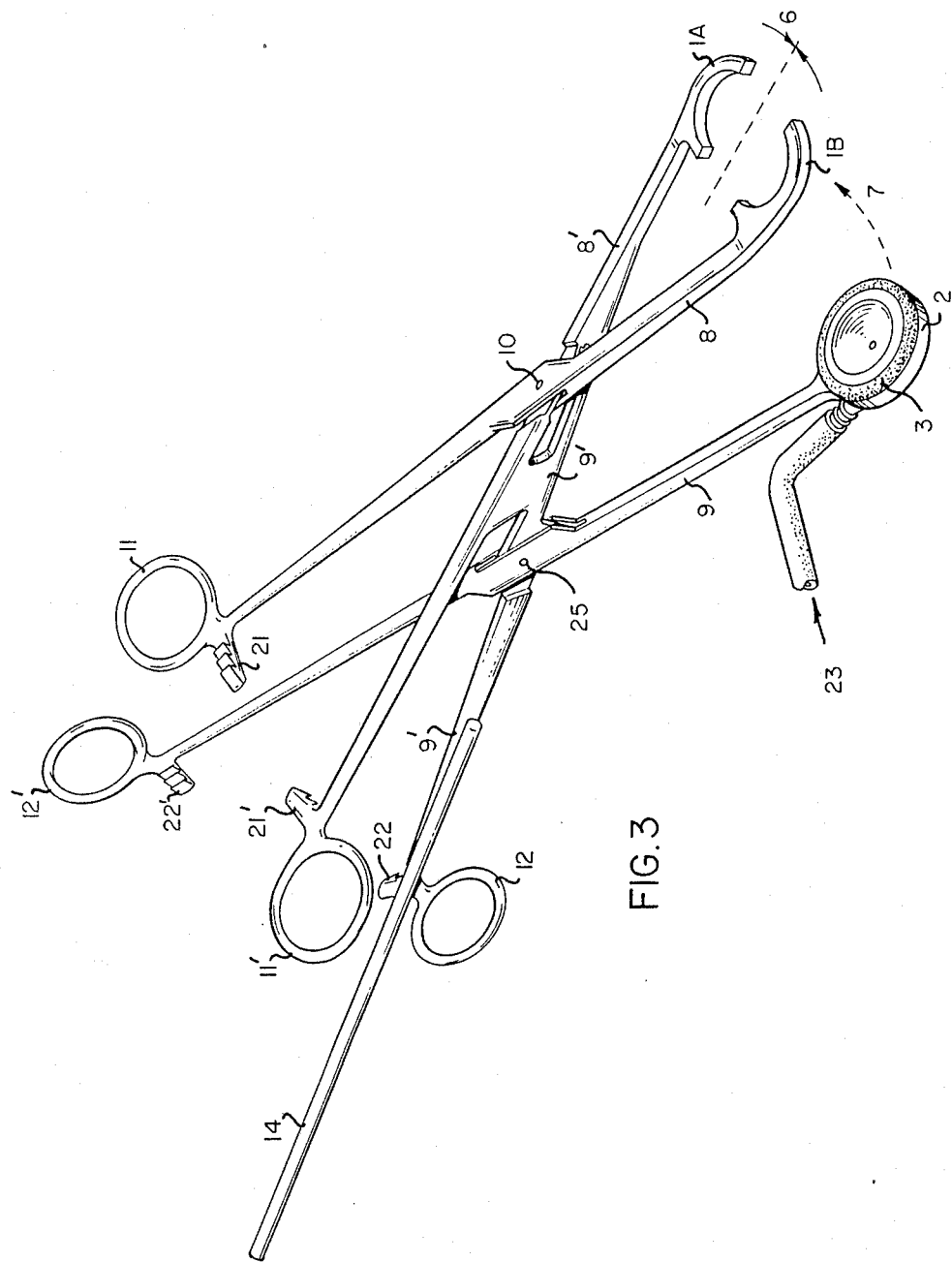
FIG. 3 is a perspective view of the invention.
Figure 4:
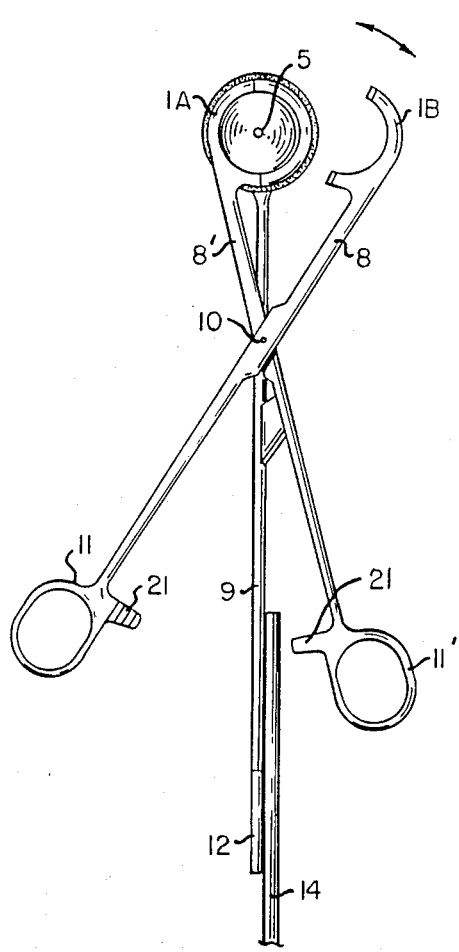
FIG. 4 is a top view of the invention.
Figure 5:
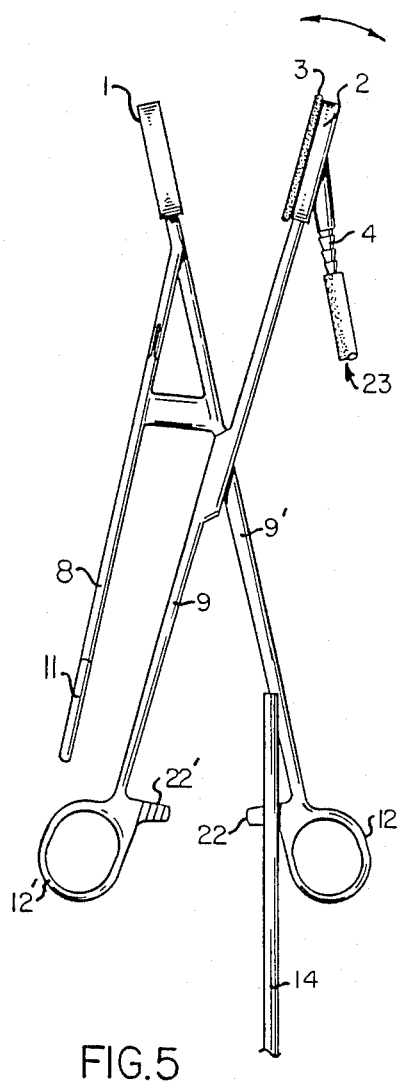
FIG. 5 is a side view of the invention.

The apparatus for applying the above-described closing and sealing forces is shown in FIG. 3. The split toroidal ring 1A–1B is mounted on the arms 8 and 8' of a locking-type forceps which is pivoted at 10 and terminates in the fingerholds 11 and 11' and the locking tabs 21 and 21'. The chamber 2 is mounted on one arm 9 of a second locking forceps which is pivoted at 25 and terminates in the fingerholds 12 and 12' and the locking tabs 22 and 22'. The second arm 9' of the second forceps is welded or otherwise attached to the underside of arm 8'. A holding rod 14 is attached to arm 9' near fingerhold 12. With this construction, pressure in the fingerholds 11 and 11' closes the toroidal ring segments 1A and 1B around the wall of the tube. Pressure on the fingerholds 12 and 12' now moves the chamber 2 orthogonally (direction 7) to the plane of the now-closed toroidal ring segments and causes the flexible sealing ring 3 to seat on the side of the closed ring with wall 20 (FIG. 2a) between. The rod 14 may be supported by a standard laboratory clamp and serves to hold the invention as well as the organ being injected. The injectate 23 is introduced through a hose coupled to the serrated inlet pipe 4. The physical relation between the arms 8 and 8' and the arms 9 and 9' and the holding rod 14 is also shown in the top and side views of FIG. 4 and FIG. 5 respectively.

Figure 2B:
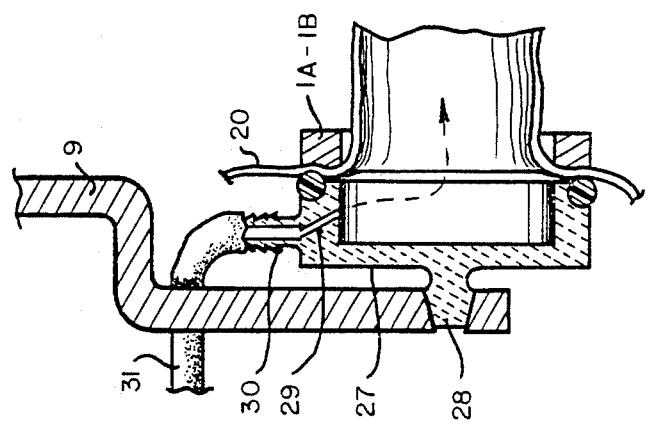
FIG. 2b is a cross sectional view of a second embodiment of the clamping and injection elements.

In FIG. 2b is shown another embodiment of the clamping and injection element. A disposable chamber 27 is made of plastic and is detachably joined to the arm 9 through the tapered joint 28. The inlet tube 30 is cemented at one end to the chamber 27 and serrated at the other end to receive the flexible tubing 31. The inlet opening for injection 29 is drilled in one wall of the chamber. After the injected liquid has hardened, the ring segments 1A and 1B are separated and the flexible tubing 31 is removed. The entire chamber 27 can then be removed from the apparatus along with the replica and cut off at any desired point. The disposable chamber is advantageous when certain hardenable liquids which have poor mold release characteristics are used.

Two injection clamps made according to the present invention would be used for the simultaneous and selective injection of the right and left coronary arteries, for example, each with a different color injectate.

After the liquid has hardened the apparatus is removed and the organ with the injected blood vessels is immersed in an acid or alkali bath until the organic tissues are corroded away.

The present invention is applicable to all systems of biologic organs having an incoming or exiting blood vessel or duct—for example: cardiovascular, pulmonary, renal, gastrointestinal, genitourinary and neurologic. Organ sources include mammals, birds, reptiles, amphibians and fish.

The invention is constructed of injectate-resistant material. The hardening liquid may be any castable substance. The locking forceps may be replaced by other types of clamps or holding devices. These and other variations are possible while keeping within the spirit of the present invention.

What is claimed is:

1. An apparatus for producing anatomically accurate and complete casts of blood vessels and ductal organs of animals from a hardenable material, said apparatus comprising:
    a lockable clamping means capable of encircling a selected blood vessel or ductal organ tissue, said clamping means including a pair of edge-mated, semi-circular segments of a split toroidal ring, each segment being mounted on a respective end of a leg of a first locking forceps to form a tissue encircling ring;
    a sealing means mounted on one leg of a second locking forceps, said forceps being rigidly joined to the first forceps such that the sealing means is movable orthogonally relative to the clamping means, said sealing means including an injection opening through which the hardenable material is fed to the tissue, said sealing means cooperating with the clamping means to confine a circumferential portion of the tissue around an opening of the tissue so as to provide a leak-tight entrance into said tissue; and
    injection means for feeding hardenable material to said sealing means.

2. An apparatus according to claim 1, wherein the clamping ring segments each have a flat, polished side facing the sealing means.

3. An apparatus according to claim 1, wherein the sealing means comprises a cup having a conical inside surface, the injection opening extending through a bottom of the cup, the cup further having an open end opposite the injection opening, a wide lip surrounding the open end, a flexible sealing ring disposed in said lip, and an injection inlet pipe connecting the injection means to the injection opening.

4. An apparatus according to claim 1, wherein the sealing means comprises a cup removably mounted on the second forceps, said cup having a cylindrical side wall through which said injection opening extends, a flat closed bottom, an open end opposite said bottom, a flexible sealing ring surrounding said open end, and an injection inlet pipe connecting the injection means to the injection opening.

5. An apparatus according to claim 4, wherein the cup has a tapered joint extending outwardly from the bottom opposite said open end, said one leg of said second forceps having a hole through which the tapered joint is detachably received.

* * * * *